United States Patent [19]

Alexanian et al.

[11] Patent Number: 5,344,965
[45] Date of Patent: Sep. 6, 1994

[54] PREPARATION OF A NOVEL DIISOCYANATE FROM NORBORNADIENE

[75] Inventors: Vazken A. Alexanian, Darien, Conn.; Laurence J. Nummy, Newburgh, N.Y.

[73] Assignee: Cytec Technology Corp., Wilmington, Del.

[21] Appl. No.: 110,044

[22] Filed: Aug. 20, 1993

Related U.S. Application Data

[63] Continuation of Ser. No. 303,412, Jan. 30, 1989, abandoned, which is a continuation of Ser. No. 926,071, Nov. 3, 1986, abandoned.

[51] Int. Cl.$^5$ ............................................. C07C 249/00
[52] U.S. Cl. ................................... 560/354; 560/115; 560/345
[58] Field of Search .......................................... 560/354

[56] References Cited

U.S. PATENT DOCUMENTS

| | | | |
|---|---|---|---|
| 3,454,393 | 7/1969 | Müller | 560/354 |
| 3,625,986 | 12/1971 | Feldman | 560/354 |
| 3,870,739 | 3/1975 | DeLaMater | 560/345 |
| 3,962,302 | 6/1976 | Rosenthal | 560/345 |

OTHER PUBLICATIONS

Sasaki, J. Org. Chem., 37, pp. 2317–2320 (1972).

Primary Examiner—Michael L. Shippen
Attorney, Agent, or Firm—Michael J. Kelly; Bart E. Lerman; Claire M. Schultz

[57] ABSTRACT

Novel bicyclic alkyl dicarbamates are prepared from norbornadiene and other simple starting materials, and these are subsequently thermally cracked to novel diisocyanate norbornyl derivatives, which are, among others, useful for crosslinking active hydrogen compounds.

1 Claim, No Drawings

PREPARATION OF A NOVEL DIISOCYANATE FROM NORBORNADIENE

This is a continuation of co-pending application Ser. No. 07/303,412, filed Jan. 30, 1989, now abandoned which is a continuation of application Ser. No 06/926,071, filed Nov. 3, 1986, now abandoned.

FIELD OF THE INVENTION

The present invention relates to a novel process for preparation of novel aliphatic carbamates or diurethanes from the starting material norbornadiene. The diurethane compounds can be cracked to obtain novel aliphatic tricyclic diisocyanate compounds. These tricyclic diisocyanates are useful by mixing with diols and polyols to produce polyurethanes either as films for coating applications, thick sections for light stable RIM elastomers, or foams for use in polyurethane foams.

BACKGROUND OF THE INVENTION

Conrad and Hock, Formaldehydderivate der Urethane, Berichte, 36, 2206 (1903) disclose the condensation reaction of formaldehyde and the ethyl ester of carbamic acid or urethane to produce methylene diurethane (MEDU), a compound of the formula

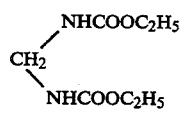

Sasaki et al., J. Org. Chem., 37, 14 (1972), disclose that norbornadiene can be heated in benzene solution with methylenebisurethane in the presence of boron trifluoride etherate to produce a mixture of carbamates including the tricyclic ethyl ester

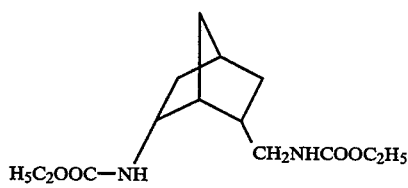

There is no suggestion however, that the tricyclic ethyl ester or any other ester can be cracked to yield useful tricyclic diisocyanates.

It has been discovered now that diisocyanate norbornyl derivatives can be prepared using inexpensive starting materials, for example norbornadiene, formaldehyde and methyl carbamate to produce novel norbornyl carbamates. These novel carbamates can in turn, be cracked to yield new and useful diisocyanate norbornyl derivatives, heretofore unobtainable in this way from the prior art. The novel products lack many of the disadvantages of the prior art. In particular, they have high reactivity, light stability and selectivity.

SUMMARY OF THE INVENTION

According to the present invention, there is provided a process for the preparation of a diurethane of the formula:

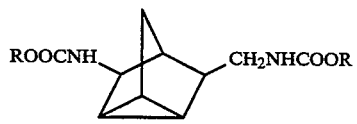

wherein R is alkyl of from about 1 to about 30, preferably from 1 to 18 carbon atoms, said process comprising reacting
  (a) an unsaturated bicyclic hydrocarbon of the formula

with
  (b) a methylene-bis-alkylcarbamate of the formula

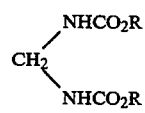

wherein R is as defined above, in the presence of:
  (c) an effective catalytic amount of an acid at a temperature of from about 40° C. to about 150° C. until formation of said urethane compound (I) is substantially complete.

Also contemplated by the present invention are urethane compounds of the formula:

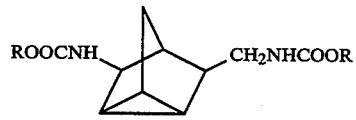

wherein R is alkyl of from about 1 to about 30, preferably 1 to 18 carbon atoms.

Also contemplated herein is a process for production of an isocyanate compound of the formula

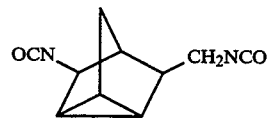

said process comprising heating a diurethane of the formula

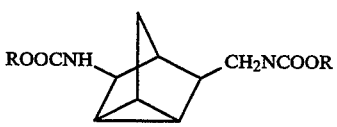

wherein R is alkyl of from about 1 to about 30, preferably 1 to 18 carbon atoms, at a temperature of from about 150° C. to about 700° C. until formation of said diisocyanate compound (IV).

Also provided in accordance with this invention are compounds of the formula:

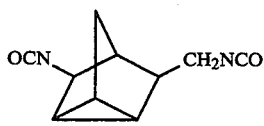

Among the features of this invention are curable compositions comprising:

(i) active hydrogen compounds, especially polyols, preferably hydroxy functional polyacrylates or polyesters; and (ii) the novel diisocyanate above defined.

Other objects and advantages of the present invention will become apparent from the following detailed description of the invention taken in conjunction with the illustrative working examples.

DETAILED DESCRIPTION OF THE INVENTION

Useful as a starting material in accordance with the present invention is norbornadiene or bicyclo [2.2.1] hepta-2,5-diene, the compound of formula (II):

The compound can be made by those skilled in this art, and it is also available commercially, e.g., from Aldrich Chemical Company.

The other starting materials, namely, the compounds of formula (III)

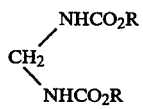  (III)

wherein R is alkyl of from 1 to 30, preferably 1 to 18 carbon atoms, straight chain and branched, e.g., methyl, ethyl, propyl, 2-ethylhexyl, n-octadecyl, triacontyl, and the like, also can be produced in known ways, e.g., by the technique described by Conrad et al. above, using suitably substituted alkyl esters of carbamic acid. Instead of gaseous formaldehyde or aqueous formaldehyde, a formaldehyde precursor, such as trioxymethylene, paraform, formcel, and the like can be used. Preferably in the methylene bisalkyl carbamate (III) R is methyl.

To carry out the condensation between (II) and (III) it is necessary to heat the components in the presence of an acidic catalyst. In accordance with this invention the preparation of the aliphatic tricylic urethane ester takes place at temperatures from 40° C. up to 150° C. in the presence of an acid such as boron trifluoride, sulfuric acid, toluene sulfonic acid, dodecyl benzene sulfonic acid, hydrocarbon sulfate esters, hydrochloric acid, and other Lewis and Bronstead acids. The preferred catalyst is boron trifluride etherate. The reaction can take place in the absence of solvent or in the presence of solvents such as methylene chloride, toluene, xylene, chlorobenzene, and the like.

As will be obvious to those skilled in this art, the alkylene-bis-alkylcarbamate (III) can be generated in situ either by pre-reacting formaldehyde or a formaldehyde precursor with the alkyl carbamate or by reacting a mixture comprising formaldehyde, the alkyl carbamate and norbornadiene.

The proportion of methylene bis-carbamic acid ester to norbornadiene is near to stoichiometric. Typically, in running the condensation reaction between (II) and (III), other by-products in addition to the desired dicarbamate norbornyl derivative will be produced. These by-products are obtained as volatile fractions and comprise monourethane compounds of the following formulae:

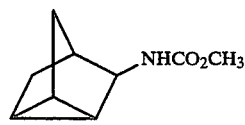

and

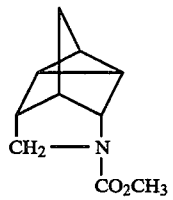

It is desirable to separate the dicarbamate (I) from these by-products prior to thermal cracking. Such separation can be achieved by techniques known to those skilled in the art, for example, by distillation, as will be exemplified hereinafter. In any event, the preferable amount of (III) with respect to (II) is a stoichiometric amount.

Because norbornadiene is a reactive compound, sparing amounts of catalyst can be employed to effect condensation of the two reactants. In any event, the amount of catalyst required to promote the addition of norbornadiene and methylene-bis-carbamate is not critical and can be varied widely. The amount is typically from 0.05 to 50 mole % and preferably about 0.10 to 5 mole %.

Preferably the catalyst is dissolved or suspended in the warm reaction mixture and the norbornadiene is slowly added. When the reaction is complete, the time generally being from about 2 hours to about 4 hours, the mixture is treated to remove or neutralize the catalyst. Then the unreacted materials and solvent, if used are removed, e.g., by distillation leaving the polycyclic product of formula (I) as a residue. Purification can be effected, e.g., by column separation using, e.g., methylene chloride, as an eluent.

The aliphatic polycylic bis urethanes (I) form the corresponding isocyanates (V) by thermal cracking while splitting off the corresponding alkanol. With norbornadiene used as the starting material, the ultimate compound is of the formula:

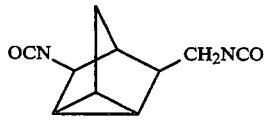

In many cases the alcohol, preferably methanol, can usefully be recycled with urea or isocyanic acid to form methyl carbamate which is then reacted with formaldehyde or a formaldehyde precursor to form compound (III).

In cracking the urethane esters (I) to form the corresponding isocyanates (IV) the acidic catalyst must be removed or neutralized, for example, with calcium oxide, sodium carbamate, sodium hydroxide and the like, which is followed by cracking of the bis-urethane either solvent-free or in high boiling solvents, such as hexadecane, diphenyl ether, diisopropyl naphthalene and the like. Cracking takes place at temperatures on the order of 150° C. to 700° C., preferably 400° C. to 600° C. splitting off the alcohol to yield the corresponding isocyanates. Pressures can vary widely, but it is convenient to use between about 30 and about 50 mm of mercury.

In cracking the diurethanes, monoisocyanate-monourethane compounds may contaminate the cracked reaction mixture comprising the desired diisocyanate. These hybrid by-products can likewise be separated from the diisocyanate by methods well-known to those skilled in the art, e.g., distillation, as will be exemplified in the next section.

Because of their unique tricyclic structure the diisocyanates of this invention have excellent physical properties when used as crosslinkers with polyester polyols, polyether polyols, and the like, to make polyurethanes useful in coating applications. They are characterized by high reactivity, light stability, high selectivity, and low toxicity as a result of combining a primary and a secondary isocyanate in a single non-aromatic compound.

In accordance with known techniques coating compositions can be made by mixing polyols with effective amounts 0.5-5 —NCO/—OH of the diisocyanates optionally in a hydrocarbon solvent, preferably with a catalyst, e.g., 1 percent of a tin compound, and curing, e.g., at 60°-150° C. for 1 minute to 1 hour. Hard, solvent-resistant coatings are thus obtained.

DESCRIPTION OF THE PREFERRED EMBODIMENTS

The following examples illustrate the novel processes and novel compounds of the present invention. They are not to be construed to limit the claims in any manner whatsoever.

In the following Examples, the following abbreviations are used:

MEDU—methylene diurethane
NBDU—3-N-methoxycarbonylamino-5-N-methoxycarbonylaminomethyltricylco (2.2.1.0$^{2,6}$)
NBDI—Isocyanato-5-isocyanato-methyltricyclo (2.2.1.0$^{2,6}$) heptane

EXAMPLE 1

(a) Preparation of NBDU

In a flask are reacted 162 g, 1 mol of MEDU and 92 g, 1 mol of norbonadiene in the presence of 17 g, 0.12 mol of boron trifluoride etherate catalyst for 3 hours at a temperature of approximately 110° C. The reaction mixture was continuously refluxed during this period using toluene solution. Analysis indicated that the products, obtained in 38.5% yield comprised NBDU in 23% yield (52 g) and approximately equal weights of two by-products of the formulae:

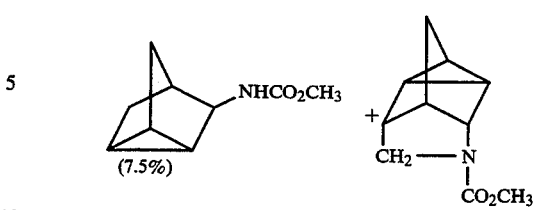

The byproducts were isolated from NBDU by a simple vacuum distillation. The by-products were removed as volatile fractions, b.p. 120°-160° C./0.2 mm Hg. Methanol treatment of the distillate provided the diurethane, NBDU, with a purity of approximately 70% as determined by GLC. Pure samples of NBDU were prepared by column separation on silica gel absorbent, using methylene chloride as eluent.

(b) Preparation of NBDI

The diurethane product of step (a), substantially free of by-products, 25.4 g, 0.10 mol, was cracked in a hot tube, using a standard 17×1¼ inch column at 500° C. packed with stainless steel Propack 316SS packing, under a pressure of 40 mm Hg, nitrogen bleed and a 5 g/hr feed rate. Analysis indicated that the products, obtained in 95% yield, comprised NBDI (63% yield, 12 g), and an isomeric mixture of monoisocyanate-monourethane by-products of the formulae:

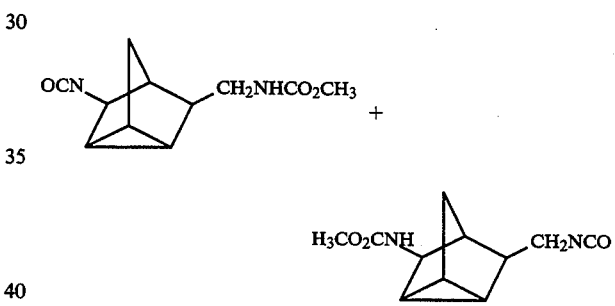

The crude product, comprising predominantly NBDI was doubly distilled at 90°-92° C., 0. 1 mm Hg to obtain NBDI in a 32% yield, 90.5% pure by GLC which conformed well with purity that was determined by NCO titration.

EXAMPLE 2

A curable composition is made comprising a hydroxy functional acrylic acid and the NBDI of Example 1. A copolymer of hydroxyethyl acrylate with other acrylics (G-CURE® 867) and NBDI at 50 percent non-volatiles in a hydrocarbon solvent, the —NCO/—OH ratio being 1.1/1.0 was treated with 1.0 percent (TRS) of a tin catalyst, UL-28, and spread on a 1200 S aluminum substrate and cured for 20 minutes at 60°, 80° and 100° C. All of the systems advanced within 1 day at room temperature to a hard, solvent-resistant film.

EXAMPLE 3

A curable composition is made comprising a hydroxy functional polyester and the NBDI of Example 1. The hydroxy functional (MULTRON® 221-75) and NBDI at 60 percent non-volatiles in a hydrocarbon solvent, the —NCO/—OH ratio being 1.1/1.0, was treated with 1.0 percent (TRS) of a tin catalyst, UL-28, and spread on a 1200 S aluminum substrate and cured 20 minutes at 60°, 80° and 100° C. All of the systems advance within 7 days at room temperature to a hard, solvent-resistant film.

The above-mentioned publications are incorporated herein by reference.

Many variations will suggest themselves to those skilled in the art in light of the above detailed description. For example, instead of sulfuric acid catalyst, boron trifluoride-ether complex, phosphoric acid and sulfuric acid can be used. Instead of solvent-free cracking, cracking in hexadecane, a high boiling solvent can be used. Instead of using MEDU, a mixture of paraformaldehyde and methyl carbamate can be used. All such obvious variations are within the full intended scope of the appended claims.

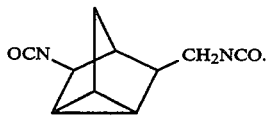

We claim:

1. A diisocyanate compound of the formula: